(12) United States Patent
Shen-Chih et al.

(10) Patent No.: US 6,843,990 B2
(45) Date of Patent: Jan. 18, 2005

(54) MONOCLONAL ANTIBODIES FOR THE DETECTION OF DECOY RECEPTOR 3, HYBRIDOMAS PRODUCING SAID ANTIBODIES AND USES THEREOF

(75) Inventors: Mai Shen-Chih, Taipei Hsien (TW); Liu Shih-Jen, Taipei Hsien (TW)

(73) Assignee: Anawrahta Biotech Co., Taipei (TW)

( * ) Notice: Subject to any disclaimer, the term of this patent is extended or adjusted under 35 U.S.C. 154(b) by 162 days.

(21) Appl. No.: 09/998,196

(22) Filed: Dec. 3, 2001

(65) Prior Publication Data

US 2002/0068064 A1 Jun. 6, 2002

(30) Foreign Application Priority Data

Dec. 5, 2000 (TW) ........................................ 89125856 A

(51) Int. Cl.$^7$ ............................................ A61K 39/395
(52) U.S. Cl. ................ 424/178.1; 424/130.1; 424/138.1; 424/139.1; 424/141.1; 424/143.1; 424/155.1; 435/326; 435/328; 435/330; 435/331; 435/334; 530/350; 530/387.1; 530/387.3; 530/387.7; 530/387.9; 530/388.22; 530/391.3
(58) Field of Search .............................. 530/350, 387.1, 530/387.3, 387.7, 387.9, 388.22, 391.3; 435/326, 328, 330, 331, 334; 424/130.1, 138.1, 139.1, 141.1, 143.1, 155.1, 178.1

(56) References Cited

PUBLICATIONS

Stites et al. (1994) Basic and Clinical Immunology, 8$^{th}$ Ed. (Appleton &Lange:Norwalk, CT), pp. 316, 317, 412–414.*
Littaua et al., Human IgG Fc receptor II meidates antibody–dependent enhancement of dengue virus infection, J. Immunol. 144(8):3183–3186, Apr. 15, 1990.*

Yoshikawa et al., Human monoclonal antibody reactive to stomach cancer produced by mouse–human hybridoma technique, Jap. J. Cancer Res. 77(11):1122(abstract), Nov. 1986.*

Yu, K.Y. et al., "A Newly Identified Member of Tumor Necrosis Factor Receptor Superfamily (TR6) Suppresses LIGHT–mediated Apoptosis," J. Biol. Chem. 274(20):13733–13736, 1991.

Sheikh, M.S. et al., "Death and Decoy Receptors and p53–mediated Apoptosis," Leukemia 14:1509–1513, 2000.

Green, Douglas, "Death Deceiver," Nature 396–629–630, 1998.

Pitti, Robert M. et al., "Genomic Amplification of a Decoy Receptor for Fas Ligand in Lung and Colon Cancer," Nature 396:699–702, 1998.

Chang B. et al., "Overexpression of M68/DcR3 in Human Gastrointestinal Tract Tumors Independent of Gene Amplification and Its Location in Four–Gene Cluster," PNAS 97(3):1230–1235, 2000.

* cited by examiner

Primary Examiner—Lorraine Spector
Assistant Examiner—Claire M. Kaufman
(74) Attorney, Agent, or Firm—Fish & Richardson P.C.

(57) ABSTRACT

The invention provides monoclonal antibodies against decoy receptor 3 (DcR3), hybridomas producing said antibodies, kits containing said monoclonal antibodies and uses of the hybridomas, antibodies and kits for the detection of DcR3–associated diseases, as well as for the treatment and/or prevention of DcR3–associated diseases.

20 Claims, 4 Drawing Sheets

MONOCLONAL ANTIBODIES FOR THE DETECTION OF DECOY RECEPTOR 3, HYBRIDOMAS PRODUCING SAID ANTIBODIES AND USES THEREOF

FIELD OF INVENTION

The invention is directed to monoclonal antibodies against decoy receptor 3 (DcR3), hybridomas producing said antibodies, kits containing said monoclonal antibodies and uses of the hybridomas, antibodies and kits for the detection of DcR3-associated diseases, as well as for the treatment and/or prevention of DcR3-associated diseases.

BACKGROUND OF INVENTION

Proteins belong to the family of tumor necrosis factor and receptor thereof (TNF/TNFR) play an important role in various complicated biological modulating systems such as, for example, cell proliferation and differentiation, cell viability and death, production of cellular hormones and activation of immune cells, and etc. Among the family, there are several members which are particularly involved in the transmission of apoptosis signals and the modulation of immune system. Most of the members classified in the TNF receptor superfamily contain a death domain and are capable of transferring death signals. These members include TFNR-1, CD95/Fas/APO-1, DR3/TRAMP/APO-3, DR4/TRAIL-R/APO-2, DR5/TRAIL-R and the like. The superfamily shares a common molecular structure. Namely, they all possess a region containing from 3 to 6 repeating cycteines in their extracellular domain and they have similar amino acid sequences. In addition, these death receptors are also characterized in a conserved death domain consisting of about 80 amino acid residuals at their carboxyl terminal (Yu K. Y., et al., 1991, J. Biol. Chem. 274 (20): 13733–13736). It is known now that such a signal sequence is required and crucial in the transmission of death signals. The death domain will activate a series of pro-apoptotic protease caspase, leading the cell to apoptosis due to disruption of chromosome DNAs (Sheikh, M. S. and Fornace, A. J. Jr., 2000, Leukemia 14: 1509–1513; Douglas R. Green, 1998, Nature, 396: 629–630).

Recently, Avi Ashkenazi et al. (Nature, 396: 699–703, 1998) have found a new receptor member, DcR3/TR6, by searching the EST database. It has been found that the messenger RNA (mRNA) of decoy receptor 3 (DcR3) are expressed especially in lung tissue, rectum adenocarcinoma and certain endothelial cell lines. The expression of DcR3 mRNA is also induced in PMA/inomycin-stimulated Jurkat cell line. DcR3 contains 4 regions rich in cystein and it is a soluble protein. It is also found that DcR3 binds with FasL/CD95L and thereby inhibits the cytotoxic effect modulated by LIGHT and FasL/CD95L (Yu K. Y., et al., supra.). It is known that LIGHT is a ligand of HVEM/TR2 and LT β R highly expressed on activated T-cells and macrophages and that it leads certain adenocarcinoma cell lines to apoptosis by the signal transmission of LT β R. In addition, in the immune responses, several aspects of apoptosis are performed by the FasL-Fas system. For example, the control of peripheral clonal deletion and clonal expansion, as well as the modulation of cytotoxic T-cell activity and the like are all co-modulated by Fas and its ligand FasL. The study of Robert M. Pitti, et al. (Nature, 396: 699–702, 1998) has shown that DcR3 competes with Fas for the binding of FasL to inhibit the death signal transmitted by FasL. It is therefore suggested that certain tumour cells may avoid the attack of immune system by expressing large amount of DcR3.

The gene of DcR3 is first isolated from cells of human lung carcinoma and colon carcinoma and it is shown to be expressed in the carcinoma tissue of the alimentary canal. Chang, B. et al. (PNAS, 97(3): 1230–1235, 2000) has produced antibodies with DcR3 fragments and used the antibodies as an assay of tissue immunostaining. However, in the above reference, only polyclonal antibodies against DcR3 are produced for immunostaining and only the expression amounts of mRNA are shown. Therefore, it is not an ideal assay with respect to the specificity of the antibodies, as well as to the time and cost of detection. Moreover, the above reference fails to specifically indicate whether DcR3 exists in serum. It fails to disclose methods applicable to the clinical diagnosis of diseases either.

For the detection of diseases, especially of diseases related to cancers, there is a need for a fast, efficient and accurate method of detection to easily screen patients at early stages of cancers so that they can be subjected to more detailed examinations or further treatments at such early stages. In addition, with respect to high-risk groups having family histories of certain diseases and patients recovered from cancers, an easy, convenient, fast and accurate detection method can efficiently trace certain diseases on a regular base, so as to achieve early treatment with early detection. Enzyme-linked immunosorbent assay (ELISA) has been broadly applied in the detection of various diseases. The accuracy of the assay correlates closely with the antibody developed. Therefore, there is a pressing need for the search of a index protein capable of detecting multiple cancers and for the development of relevant detection kits therewith.

SUMMARY OF INVENTION

In view of the above, the first aspect of the invention provides a monoclonal antibody against decoy receptor 3.

The second aspect of the invention provides a hybridoma producing said monoclonal antibody.

The third aspect of the invention provides a fusion protein comprising a decoy receptor 3 and an immunoglobulin constant region fragment, as well as a pharmaceutical composition comprising said fusion protein.

The fourth aspect of the invention provides a kit for the detection of diseases associated with decoy receptor 3, said kit comprising: (i) a monoclonal antibody produced by hybridoma 9A10C3 specifically against decoy receptor 3 and another monoclonal antibody produced by hybridoma 3H5 specifically against decoy receptor 3; (ii) a means of support, on which attached said monoclonal antibody produced by hybridoma 9A10C3 specifically against decoy receptor 3; (iii) a washing solution; and (iv) a means for signal generation, which can be operably linked with said monoclonal antibody produced by hybridoma 3H5 specifically against decoy receptor 3 to produce a signal.

The fifth aspect of the invention provides a method for the determination of decoy receptor 3 level, said method comprising steps: (a) providing a monoclonal antibody produced by hybridoma 9A10C3 specifically against decoy receptor 3; (b) attaching said monoclonal antibody on a means of support to form an antibody-support conjugate; (c) contacting a detection sample or the decoy receptor 3 standard with said antibody-support conjugate; (d) washing with a washing solution; (e) providing a means for signal generation, which can be operably linked with said monoclonal antibody produced by hybridoma 3H5 specifically against decoy receptor 3 to produce a signal; and (f) determining the signal produced by said means for signal generation.

To make the above and other aspects, characteristics and advantages of the invention more apparent, a more detailed explanation is provided below with the preferred embodiments and the attached drawings as follows.

DETAILED DESCRIPTION OF INVENTION

Figure 1:
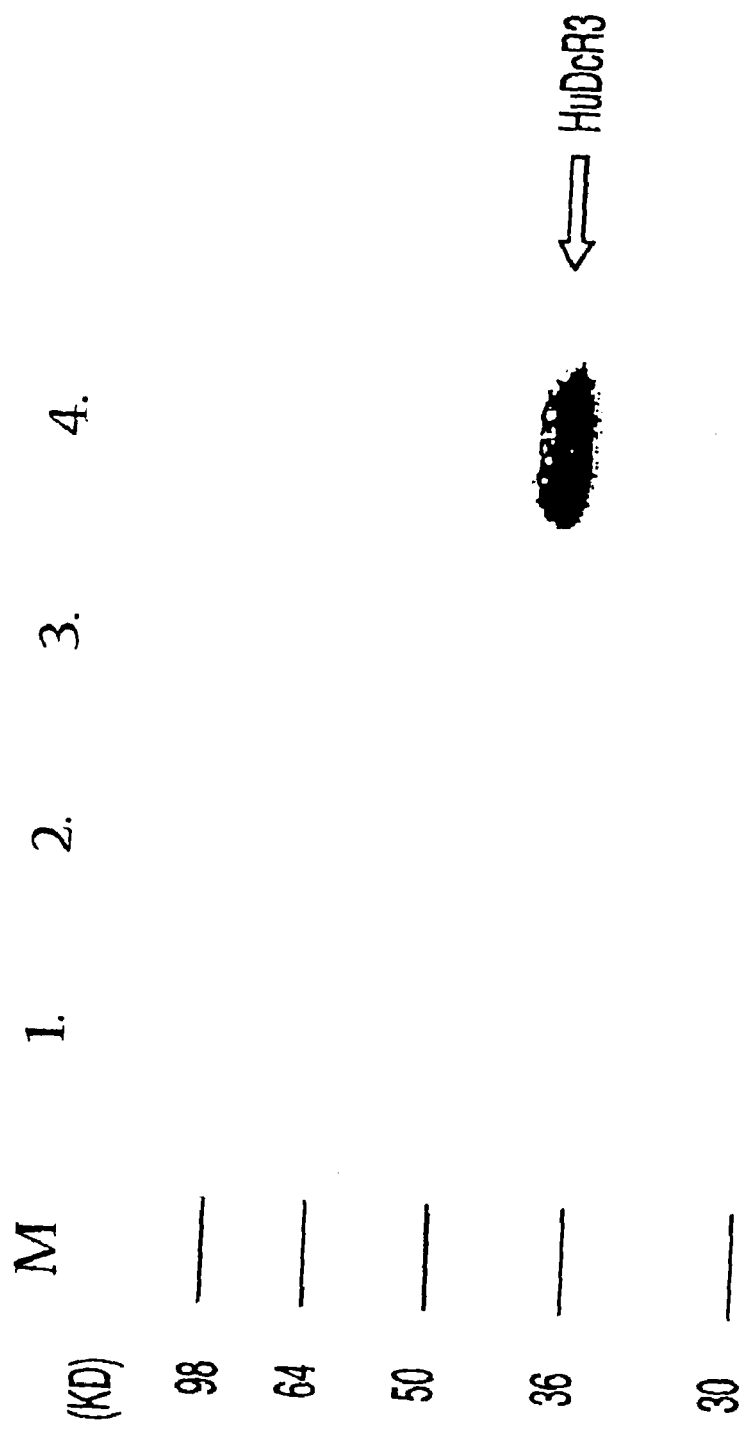
FIG. 1 is a Western blot which shows that hybridoma 9A10C3 of the invention specifically recognizes DcR3 expressed in vitro.

In view of the fact that decoy receptor 3 (referred to herein as DcR3) is expressed in specific tissues and environments, the inventors therefore developed highly specific anti-DcR3 monoclonal antibodies and screened therewith several diseases (such as various cancers, lupus erythematosus, hepatitis B, allergies and acquired immunity deficiency syndrome) so as to develop detection kits for diseases associated with DcR3 and to provide an alternate route for the early screening of serious diseases.

Utilizing gene sequences of currently available libraries, cDNA fragment of human DcR3 is amplified with polymerase chain reaction (PCR) from the human embryo lung cDNA library. The fragment is then cloned to be linked with the immunoglobulin constant region fragment (Fc) and the fusion protein DcR3-Fc is expressed in appropriate host cells. The above cloning method is well known by persons skilled in the art of biology and will be described in details in the following Examples. The fusion of DcR3 and the constant region fragment increases the solubility of the fusion protein and facilitates purification and recovering thereof after expression. In addition, it makes the fusion protein possess properties similar to antibodies to facilitate its application in other aspects. Furthermore, the fusion protein can be vehicled with appropriate carriers to form a pharmaceutical composition for use in mammals. The fusion protein can bind to FasL to inhibit death signal transmitted by the binding of Fas and FasL. Therefore, the pharmaceutical composition comprising said fusion protein as provided by the invention has potential for the treatment and/or prevention of DcR3-associated diseases. In a preferred embodiment, the constant region fragment is obtained from human G1 immunoglobulin (IgG1 Fc).

The invention uses the process of B-cell fusion to produce B-cell hybridomas 3H5 and 9A10C3 specific to DcR3. Said process uses known cell fusogenic agent such as polyethylene glycol (PEG) to fuse myeloma cell line and B-lymphocyte producing anti-DcR3 antibody. Hybridoma cell lines are selected by HAT and the specificity of the antibody in the hybridoma culture medium is analyzed with ELISA. Monoclonal hybridoma cell line specific to DcR3 is selected and then injected into the abdominal cavity of mouse to produce ascites. Enzymatic immunoassay agent is developed with said monoclonal antibody to determine the level of DcR3 in the blood. The immunogen used by the invention is the above DcR3-Fc fusion protein produced by genetic engineering, the details thereof being described in the following Examples.

Hybridoma prepared according to the invention can produce the light chain and heavy chain variable region polypeptide of the anti-DcR3 monoclonal antibody. That is, the hybridoma produces monoclonal antibody comprising the heavy chain variable region polypeptide and the light chain variable region polypeptide specific to DcR3.

The invention provides a double-antibody sandwich immunoassay for the determination of DcR3 level, which attaches the anti-DcR3 monoclonal antibody (e.g. 9A10C3) on the surface of a means of support. For the assay, different standard concentrations of DcR3 or the samples to be tested are added to the above immobilized antibody-support conjugate. A washing solution is then applied to wash away unbound samples. Another anti-DcR3 monoclonal antibody recognizing a different epitope (e.g. 3H5) is added, which can bind to a means for signal generation to produce detectable signals under appropriate conditions. Because of the characteristic of the anti-DcR3 monoclonal antibody to bind specifically to DcR3, the standard curve of signals developed from the intensities of signals generated by known standard concentrations of DcR3 can be used to determine the DcR3 level in the test blood samples. In addition, the use of two monoclonal antibodies recognizing different epitopes can substantially enhance the accuracy of the assay.

The invention also encompasses an immunoassay kit for the detection of DcR3-associated diseases, said kit comprising (i) monoclonal antibodies specific to DcR3 produced by hybridomas 9A10C3 and 3H5; (ii) a means of support, on which attached said monoclonal antibody specific to DcR3 produced by hybridoma 9A10C3; (iii) a washing solution; and (iv) a means for signal generation, which can be operably linked with said monoclonal antibody specific to DcR3 produced by hybridoma 3H5 to produce a signal.

Appropriate means of support which can be used in the invention includes microtiter plate, bead, and protein immobilizing material made with polyethylene, polystyrene, nitrocellulose or nylon. Washing solution suitable of the invention includes, but not limited to phosphate-buffered saline (PBS), Tris-buffered saline (TBS), optionally added thereto protease inhibitors such as benzamidine or surfactants such as series Tween-20, Tween-80 and the like. The means for signal generation is well known by persons skilled in the art and can be selected as needed, which includes radioactivity immunoassay, fluorescence immunoassay such as lanthanoid fluorescent agents, luminescent label such as biological luminescent label or chemical luminescent label, or enzyme. Enzymes which can be used include alkaline phosphatase (AP), horseradish peroxidase (HRP), or β-galactosidase. The use of the above enzyme can be accompanied by an appropriate substrate for visualization. The choice of substrate depends on the enzyme selected and is well within the knowledge of persons skilled in the art. Suitable substrates include p-nitrophenyl phosphate (pNPP), 2, 2'-azino-di-(3-ethylbenzthiazoline sulfonate (ABTS), 5-bromo-4-chloro-3-indolyl-phosphate/nitro-blue tetrazolium (BCIP/NBT) or naphthol AS-TR phosphate or 3,3',5, 5'-tetramethyl-benzidine and the like. See *Antibody: A Laboratory Manual*, Ed. Harlow & Dayid Lane, 1988 for methods and conditions of immunoassays.

In the preferred embodiments of the invention, the immunoassay kit for the detection of DcR3-associated diseases can take further advantage of the specific binding of biotin and avidin to amplify signal and to enhance accuracy. The monoclonal antibody provided by the invention (e.g. 3H5) is linked with biotin and subsequently used to recognize and bind to DcR3 in the samples. Avidin linked to an enzyme (such as alkaline phosphatase (AP), horseradish peroxidase (HRP), or β-galactosidase) is then added and an appropriate substrate is used for visualization. By the first recognition of monoclonal antibody 3H5 to DcR3 and the second specific binding of biotin to avidin, not only can we amplify the detection signal, but also can we substantially decrease errors.

The DcR3-associated diseases detectable by the immunoassay kit of the invention include, but not limited to cancers, such as nasopharyngeal cancer, head and neck cancer, lung cancer, breast cancer, colon cancer, transitional epithelial cancer (TCC), hepatic cancer (HCC), esophageal cancer, leukemia and the like, or lupus erythematosus, hepatitis B, autoimmunity diseases, allergies such as asthma, acquired immunity deficiency syndrome (AIDS) and the like. The results are as follows.

The fusion protein (DcR3-Fc), hybridomas and monoclonal antibodies against DcR3 provided by the invention, in addition to the application in the above detection kits, can also be used in other related immunological fields, such as flow cytometry, one-step strip, Western blot, immunoprecipitation, immunofluorescent staining, histochemical staining, in situ labeling and the like, which are all intended to be encompassed in the scope of the invention.

EXAMPLES

The invention will be further explained in details by the following examples. It should be understood that these examples are provided for the purpose of illustration only and that by no means will they constitute any limitation to the scope of the invention.

Example 1
Preparation of DcR3-Fc Fusion Protein (A) Based on the EST cDNA library, cDNA fragment of human DcR3 was amplified with PCR from the human embryo lung cDNA library. The fragment was then cloned to be linked with the Fc portion of human G1 immunoglobulin (IgG1 Fc).

(B) Cell Transfection to Introduce Expression Vectors

In a 35-mm dish, moth larva cell line Sf21 was prepared and cultured overnight. In a polystyrene tube, about 100–200 ng DNA of *Autographa california* multiple nuclear polyhedrosis virus (AcMNPV, Clontech Co.) which was made linear by enzyme digestion and about 500–1000 ng DNA of a transfer vector comprising human DcR3 gene were mixed. Equal volume of a 1.5× dilution of Lipofectin (Gibco Co.) was added and mixed. The mixture was incubated at room temperature for 15 minutes. The moth larva cell line Sf21 cultured overnight was washed twice with 2 ml culture medium without fetal calf serum (FCS), care being taken to maintain the cell monolayer. 1 ml culture medium without FCS was then added and the DNA-Lipofectin mixture was added slowly. After mixing, the cells were cultured in an incubator at 28° C. for 5 hours or overnight. 1 ml culture medium containing 10% FCS was then added and the cells were cultured for additional 48 hours. 2 ml of the culture broth was collected and stored at 4° C.

(C) Determination of the Production of Recombinant Virus

PCR was used for the determination. 10 μl culture broth of the transfected cells was first taken and 10 μg proteinase K (Sigma) was added. 10×detergent buffer A (containing 50 mM KCl, 0.45% Tween-20, 10 mM Tris-HCl, pH 8.4, 0.1 mg/ml glycin buffer and 0.45% NP-40®) was added to a total volume of 100 μl. The reaction was carried out at 60° C. for 1 hour to denature and digest viral proteins and then brought to 100° C. for 10 minutes to denature viral DNAs. 5 μl of the reaction mixture was taken for PCR.

(D) Plaque Analysis

Single viral clone was picked and titrated by plaque formation. In a 35-mm dish, $10^6$ moth larva cell line Sf21 were first prepared and cultured overnight. Culture broth was withdrawn and 200 μl virus solution ($10^{-2}$–$10^{-8}$) diluted with culture broth was dropped carefully to the center of the dish, care being taken to maintain the cell monolayer. The cells were incubated at 28° C. for 1 hour. A 2% sterile solution of low melting-point agarose gel and a solution of culture medium containing 10% FCS were prepared separately. The solutions were mixed in equal volumes at 37° C. After the completion of viral reaction, the virus solution was withdrawn and 2 ml of the agarose gel mixture was added slowly along the walls of the dish. The mixture was allowed to stand at room temperature to solidify. 1 ml culture medium containing 10% FCS was added then and the culture was incubated at 28° C. for 5–7 days until of plaques occurred. To visualize the plaques more clearly, 1 ml 0.025% (w/v) solution of Neutral Red (Sigma Co.) in PBS can be added onto the agarose gel layer. The culture was then incubated in the dark at 28° C. for 2–4 hours to stain the monolayer viable cells so that the plaques can be observed more easily by eyes.

(E) Preparation of Mid-level Virus Solution $5\times10^6$ moth larva cell line Sf21 were placed in a 75-cm$^2$ cell culture flask and cultured overnight. The culture broth was withdrawn and 1 ml virus solution diluted with culture broth was added. The culture was incubated at 28° C. for 1 hour with a gentle shaking every 15 minutes. The virus solution was withdrawn and 10 ml culture broth was added. The culture was incubated at 28° C. for 4–6 days until cells showed pathological changes after viral infection. The culture broth was collected and stored at 4° C. and −70° C., and the virus titre was determined by plaque analysis.

(F) Preparation of High-level Virus Solution

Moth larva cell line Sf21 was suspension cultivated in the culture flask from the cell density of $1\times10^5$/ml to $5\times10^6$/ml. The above mid-level virus solution was added at the virus-cell ratio of 0.1–0.2 and the culture was further incubated at 28° C. for 4–6 days. The cell-free culture broth was collected, divided into aliquots and stored at 4° C. and −70° C., and the virus titre was determined by plaque analysis.

(G) Massive Protein Expression by the Suspension Cultivation of Cells

Moth larva cell line Sf21 was suspension cultivated in the culture flask from the cell density of $1\times10^5$/ml to $1-2\times10^6$/ml. Virus solution was added at the virus-cell ratio of 1:5–10 and the culture was incubated at 28° C. for 4–6 days (for massive expression of DcR3). The culture broth was collected for protein purification.

(H) Purification of the Expressed Protein

Because of its human G1 Immunoglobulin Fc portion, the soluble human DcR3 produced by the moth larva baculovirus system can be purified by Protein A Sepharose CL-4B™, preparation thereof referred to the manufacturer's manual. After purification, the fusion protein was quantified with BCA protein analysis agent (PIERCE, Cat. No. 23225).

Example 2
Preparation of Hybridoma Producing Human DcR3 Monoclonal Antibody

50 μg fusion protein (Example 1) in a total volume of 0.2 ml was injected subcutaneously to the abdomen or back of mouse (Balb/c) periodically every three weeks. After four times of immunization, mouse was sacrificed by cervical vertebra dislocation. Spleen cells were isolated and fused with 3–5 folds of myeloma NS-1 cells. Said spleen cells were washed down by 10 ml culture broth (RPMI-1640®) without FCS and left standing in a 50-ml centrifuge tube. Given amounts of myeloma NS-1 cells were measured separately, washed twice with 10 ml RPMI-1640®, and centrifuged at 300×g for 5 minutes at room temperature. After the third and fourth washing, spleen cells contained in the upper layer of culture broth after the standing treatment were added (without the other tissues contained in the lower layer). The cells were washed together and then centrifuged at 500×g for 5 minutes at room temperature. After decanting the supernatant, cells were resuspended by the remaining culture broth. 1 ml PEG-1500 at 37° C. was added. The tube was rotated continuously for 1 minute and 2 ml RPMI-1640® was added. 8 ml of the above culture broth was added in a period of 2 minutes. The tube was rotated continuously and finally centrifuged at 300×g for 10 minutes. The supernatant was decanted and culture broth containing HAT specific selection agent (Boehringer Mannheim Co.) was added. The cells were distributed into a 96-well cell culture plate at about $2 \times 10^5$ spleen cells/well. After culturing for 7–10 days, the production of specific antibody was detected with ELISA. Culture broth containing HT specific selection agent (Boehringer Mannheim Co.) was used to replace the original culture broth, diluting two folds with every medium change and carrying out limiting dilution for the cell population.

The HAT specific selection agent described above is a reagent comprising hypoxanthine, aminopterin and thymidine and the HT specific selection agent is a reagent comprising hypoxanthine and thymidine.

Example 3
Selection of Hybridoma Producing Human DcR3 Monoclonal Antibody

100 µl per well of purified protein at 0.5 µg/ml concentration was diluted ith coating buffer and then immobilized in a 96-well culture plate (Costar Co.). After reaching at 4° C. for 16 hours, the wells were treated with phosphate-buffered saline containing 0.05% Tween-20 (PBST). After washing once with 300 µl per well, 200 µl blocking buffer was added. The reaction was carried out at room temperature for 1 hour and then washed with PBST for three times. Culture broth pre-cultivated with cell hybridoma was added. The reaction was carried out at room temperature for 2 hours and then washed with PBST for five times. A 2 000-fold dilution (PBST) of goat anti-mouse immunoglobulin G linked with horseradish peroxidase (Zymed Co.) was added. The reaction was carried out at room temperature for 1 hours and then washed with PBST for five times. 100 µl enzyme substrate visualization solution (ABTS; Sigma) was added. After visualizing for 20 minutes, the absorbance was determined at $OD_{415nm}$. Because the human DcR3 antibody of the invention may contain an anti-human G1 immunoglobulin Fc portion or an anti-human DcR3 portion, ELISAs were carried out with the two proteins respectively to select hybridomas which recognize only the human DcR3 portion but not the human G1 immunoglobulin Fc portion. The hybridomas (contained in 10% DMSO and 90% FCS) were stored at −80° C. and in liquid nitrogen and cultured with standard mammalian cell culture techniques (in RPMI 1640® containing 10% FCS supplemented with 200 mM glutamin and 50 µM β-mercaptoethanol). The hybridomas have been deposited with the China Center for Type Culture Collection (CCTCC; Wuhan University, Wuhan 430072, P. R. China). The CCTCC accession numbers for Hybridomas 3H5 and 9A10C3 are CCTCC C200112 and CCTCC C200113, respectively.

Example 4
Identification of Human DcR3 Monoclonal Antibody

Immunoprecipitation: Antibody capable of immunoprecipitating the human DcR3 in the cells is the monoclonal antibody against it.

$2 \times 10^6$ cells were suspended in 200 µl lysis buffer. The suspension was placed in ice bath for 30 minutes to break the cells and then centrifuged at 4° C. at 12,000×g to remove cellular apparatus and cell fragments. 5 µl mouse normal serum was then added and preclear treatment was carried out at 4° C. with gentle shaking for 30 minutes to remove proteins which bind to unspecific immunoglobulin in the cell lysate. 40 µl 50% (v/v) suspension of Protein A Sepharose (Pharmacia Co.) was added and reaction was carried out at 4° C. for 1 hour to precipitate immunoglobulin. The mixture was centrifuged at 500×g for 3 minutes at 4° C. The pellet was reserved and resuspended with 300 µl lysis buffer. Centrifugation was again carried out at 500×g for 3 minutes to remove Sepharose. Cell lysate previously subjected to preclear treatment was allowed to react slowly with the monoclonal antibody immunoglobulin precipitated by Protein A Sepharose at 4° C. After overnight incubation, Sepharose was precipitated by centrifugation and washed. Finally, samples were suspended in protein sample solution and subjected to protein electrophoresis at 100° C. for 5 minutes.

Example 5
Immunoassay for the Detection of DcR3

(A) Preparation of Antibody Coating Plate

Monoclonal antibody 9A10C3 of the invention was diluted to 5 µg/ml in 0.1 M carbonate-buffered saline (pH 9.6). 100 µl was used to coat the surface of each well in a 96-well microtiter plate and incubated overnight at 4° C. The plate was washed once with 0.05% Tween 20/PBS and then patted dry. 200 µl of 5% skimmed milk powder/PBS was added to each well and incubated overnight at 4° C. to block the wells. The plate was washed five times with 0.05% Tween 20/PBS, patted dry and stored for later use.

(B) Immunoassay

Figure 2:
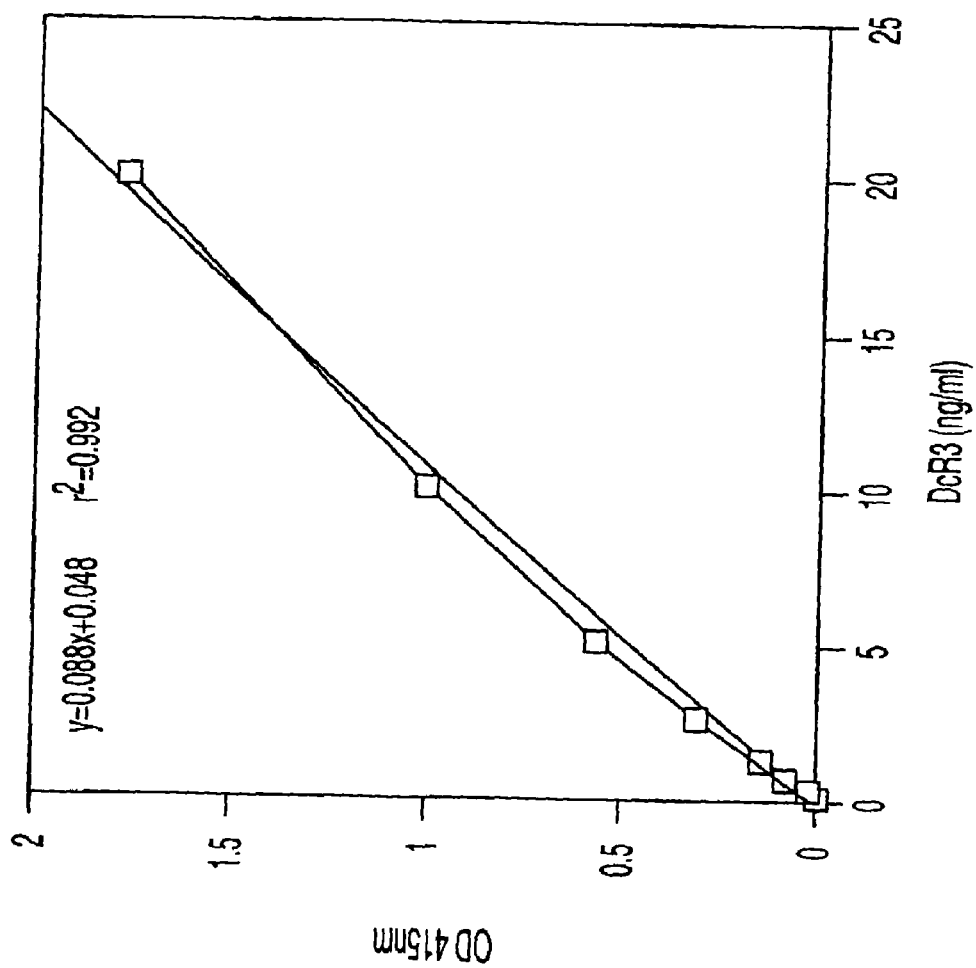
FIG. 2 is the standard quantification curve of the detection kit of the invention.
Figure 3:
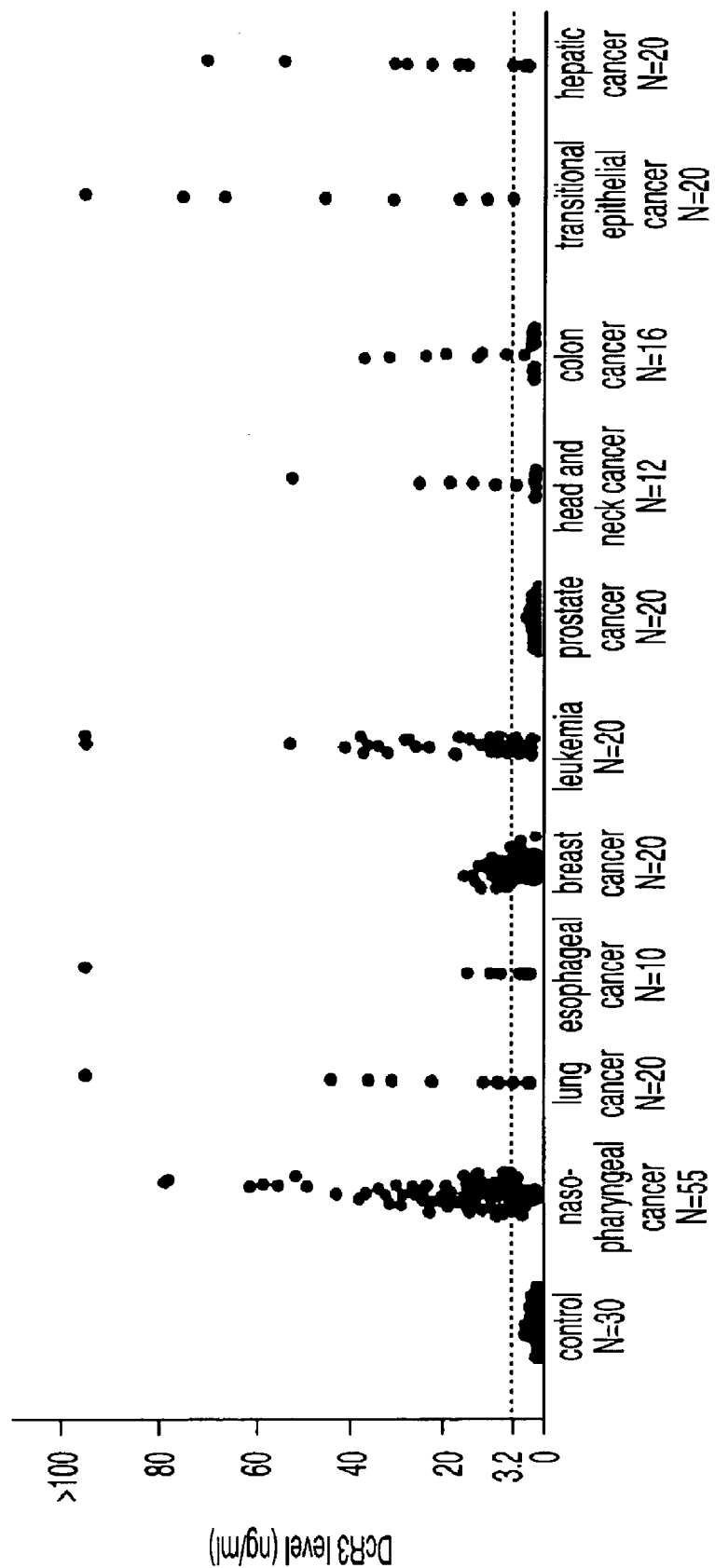
FIG. 3 shows the results obtained from assaying serum samples of patients with various cancers by the detection kit of the invention.

Test serums from patients with various DcR3-associated diseases were diluted two folds in sample dilution solution and 100 µl each was added to the wells in a 96-well microtiter plate. 100 µl DcR3 standards of different concentrations were also added to the wells. The plate was incubated at 4° C. for over 16 hours. The wells were washed five times with PBST. 100 µl biotin-labeled monoclonal antibody 3H5 was added to each well and the reaction was carried out at room temperature for 1 hour. After washing, enzyme substrate pNPP (1 mg/ml) was added and incubated at room temperature for 30 minutes for visualization. Absorbance at $OD_{415nm}$ was determined by sample reader. The standard samples included DcR3 standards of 0, 0.3125, 0.625, 1.25, 2.5, 5, 10 and 20 ng/ml and were used to plot the standard curve as shown in FIG. 2. Test serum samples included serums obtained from normal individual (control) and patients having nasopharyngeal cancer, head and neck cancer, lung cancer, prostate cancer, breast cancer, colon cancer, transitional epithelial cancer (including cancer of the urinary system such as bladder, kidney, ureter and the like), hepatic cancer, esophageal cancer, leukemia, lupus erythematosus, hepatitis B, allergies (asthma) and acquired immunity deficiency syndrome. The test results were shown in FIGS. 3 and 4.

To prove the specificity of the prepared monoclonal antibodies to DcR3, cross-reactions were carried out by the invention. With reference to FIG. 1, lane 1 represents the control (culture medium only), lane 2 is the expression vector pCR3.1-LMP (a member of the TNFR family), lane 3 contains the expression vector pCR3.1 alone, and lane 4 represents pCR3.1-DcR3. Monoclonal antibody 9A10C3 was used for the detection and the result showed that the monoclonal antibody of the invention was capable of recognizing specifically, even between members of the same family.

Figure 4:
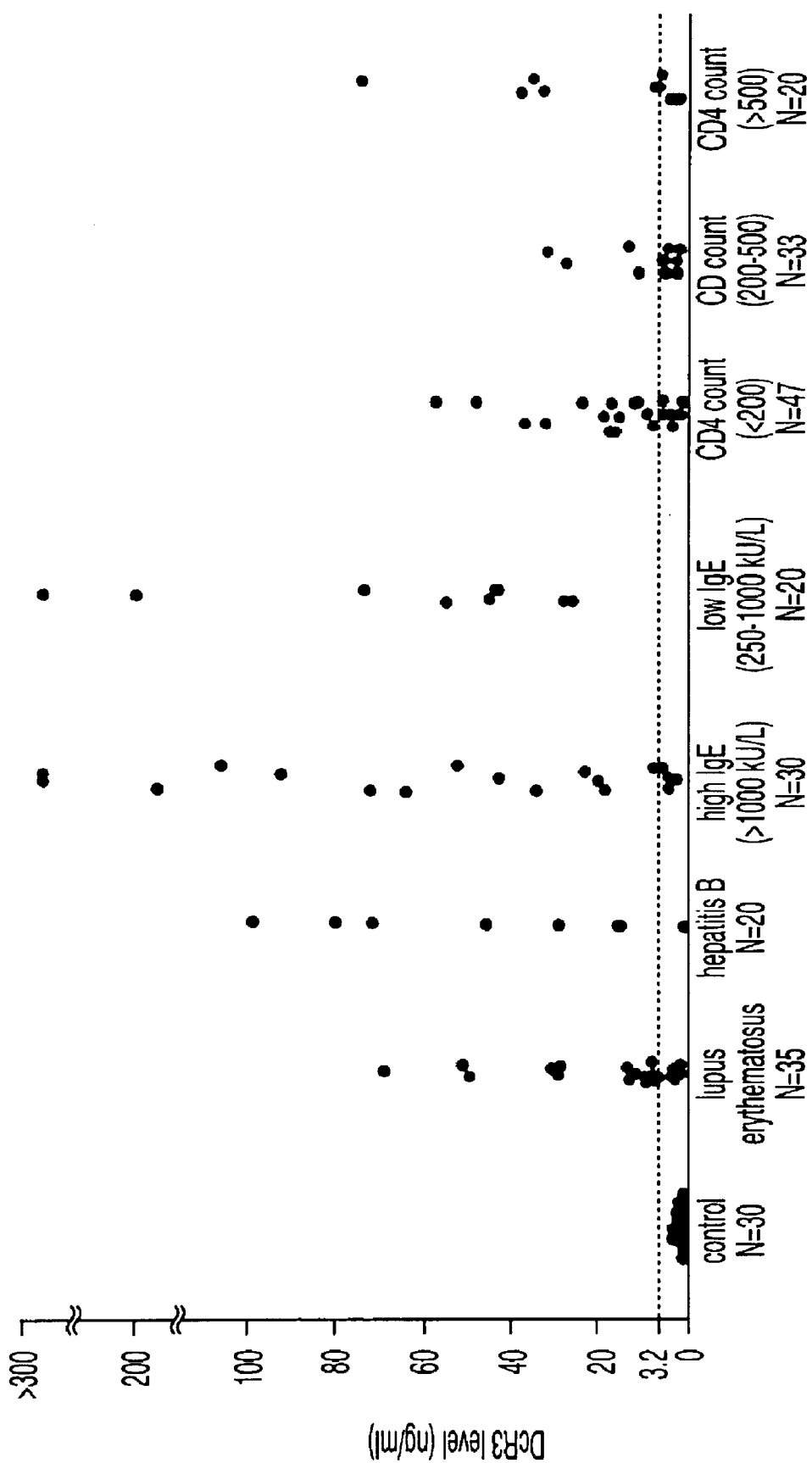
FIG. 4 shows the results obtained from assaying serum samples of patients with various non-cancer DcR3-associated diseases by the detection kit of the invention, wherein N represents the number of test samples.

The two monoclonal antibodies 3H5 and 9A10C3 were used to develop a double-antibody sandwich diagnostic kit. Higher the level of DcR3 in the samples, higher the reaction intensity was obtained (see FIG. 2). The standard curve also indicated that the sensitivity of the kit was up to 1 ng/ml. Such a double-antibody sandwich diagnostic kit can be used to determined minor quantities of DcR3. Serum samples obtained from patients with various cancers, including patients with various stages of cancer symptoms, after being assayed by the kit of the invention, all showed detectable level of DcR3 except the prostate cancer patient serum sample (see FIG. 3). In addition, samples obtained from patients with various non-cancer DcR3-associated diseases, after being assayed by the kit of the invention, also showed detectable level of DcR3 (see FIG. 4). The DcR3 concentrations detected in the control group (serum samples from normal individuals, N=30) were all under 1 ng/ml. On the other hand, if the results obtained from the test sample were higher than 3.2 ng/ml, they would be initially determined as having positive signs of the above diseases and then subjected to more detailed examinations. As shown in FIG. 4, the IgE level was classified by CAP. Asthma patient was defined as one with symptoms of trachea inflammation or allergic asthma, whose total IgE level was normally higher than 250 kU/L. The patients were further classified as high IgE level (>1,000 kU/L) and low IgE level (250–1,000 kU/L). On the contrary, the IgE level of normal individual was usually under 150 kU/L. The data indicated that in the samples obtained from asthma patients, whether they are of the group of high IgE level or low IgE level, DcR3 can be detected by the kit of the invention. Moreover, with respect to AIDS patients, current indications for its clinical diagnosis are the CD4 count and the existence of anti-HIV-1 antibody. Patient having anti-HIV-1 antibody can be further classified into three types according to the CD4 count: (1) the one whose CD4 count is over 500 is a healthy carrier and no drug administration is required; (2) the one whose CD4 count is between 200–500 requires drug administration; and (3) the one whose CD4 count is under 200 is defined as an AIDS patient. The data indicated that with respect to patients having anti-HIV-1 antibody, a DcR3 level higher than normal individuals can all detected by the kit of the invention in all of the three CD4 count types.

The above results show that the monoclonal antibody and detection kit specific to DcR3 of the invention can be used to provide an easy, convenient, fast and accurate detection method for tracing DcR3-associated diseases on a regular base, so as to achieve early treatment with early detection.

Although the invention has been described above by the preferred embodiments, these descriptions are not intended to limit the invention by any means. Variations and modifications can be made without departing from the spirit and scope of the invention by any person skilled in the art. Therefore, the protection scope of the invention can only be determined by the definitions of the appended claims.

What is claimed is:

1. A hybridoma 3H5 deposited under accession number China Center for Type Culture Collection CCTCC C200112 which produces an anti-decoy receptor 3 (DcR3) monoclonal antibody.

2. A hybridoma 9A10C3 deposited under accession number China Center for Type Culture Collection CCTCC C200113 which produces an anti-DcR3 monoclonal antibody.

3. The hybridoma of claim 1 or 2, which is a cell line produced from the fusion of a myeloma cell and a B-cell producing anti-DcR3 antibody.

4. The hybridoma of claim 3, wherein the B-cell is obtained from an animal immunized by DcR3 and an immunoglobulin constant region fragment (Fc).

5. The hybridoma of claim 4, which produces the light chain variable region polypeptide of the anti-DcR3 monoclonal antibody.

6. The hybridoma of claim 4, which produces the heavy chain variable region polypeptide of the anti-DcR3 monoclonal antibody.

7. The hybridoma of claim 4, which produced the monoclonal antibody comprising the heavy chain variable region polypeptide and the light chain variable region polypeptide specific to DcR3.

8. A kit for the detection of DcR3, said kit comprising:
(i) a monoclonal antibody specific to DcR3 produced by hybridoma 9A1OC3 deposited under accession number China Center for Type Culture Collection CCTCC C200113; and another monoclonal antibody specific to DcR3 produced by hybridoma 3H5 deposited under accession number China Center for Type Culture Collection CCTCC C200112;
(ii) a means of support, on which is attached said monoclonal antibody specific to DcR3 produced by hybridoma 9A1OC3;
(iii) a washing solution; and
(iv) a means for signal generation 1, which is operably linked with said monoclonal antibody specific to DcR3 produced by hybridoma 3H5 to produce a signal.

9. The kit of claim 8, wherein the means of support includes microtiter plate, bead, and protein immobilizing material, wherein the protein immobilizing material is selected from the group consisting of polyethylene, polystyrene, nitrocellulose and nylon.

10. The kit of claim 8, wherein the washing solution is phosphate-buffered saline (PBS) or Tris-buffered saline (TBS).

11. The kit of claim 10, wherein the washing solution further comprises a surfactant.

12. The kit of claim 8, wherein the means for signal generation is selected from the group consisting of radioactive label, fluorescent label, luminescent label, and enzyme.

13. The kit of claim 12, wherein the luminescent label is a biological luminescent label or chemical luminescent label.

14. The kit of claim 12, wherein the enzyme is selected from the group consisting of alkaline phosphatase, horseradish peroxidase and β-galactosidase.

15. The kit of claim 14, which further comprises a substrate, wherein the substrate can react with the enzyme for visulization.

16. The kit of claim 12, wherein the means for signal generation further comprises biotin.

17. The kit of claim 16, which further comprises avidin operably linked to an enzyme.

18. The kit of claim 17, wherein the enzyme is selected from the group consisting of alkaline phosphatase, horseradish peroxidase and β-galactosidase.

19. The kit of claim 18, which further comprises a substrate, wherein the substrate can react with the enzyme for visulization.

20. The kit of claim 8, further comprising a legend indicating use of the monoclonal antibody for detecting a DcR3-associated disease select from the group consisting of nasopharyngeal cancer, head and neck cancer, lung cancer, breast cancer, colon cancer, transitional epithelial cancer, hepatic cancer, esophageal cancer, leukemia, lupus erythematosus, hepatitis B, asthma, and acquired immunity deficiency syndrome.

* * * * *